(12) United States Patent
Chevalier

(10) Patent No.: US 8,207,281 B2
(45) Date of Patent: Jun. 26, 2012

(54) PROCESS FOR PREPARING TRANSITION METAL COMPOUNDS FOR OLEFINS POLYMERIZATION

(75) Inventor: Reynald Chevalier, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 48 days.

(21) Appl. No.: 12/734,266

(22) PCT Filed: Dec. 11, 2008

(86) PCT No.: PCT/EP2008/010497
§ 371 (c)(1),
(2), (4) Date: Apr. 21, 2010

(87) PCT Pub. No.: WO2009/077115
PCT Pub. Date: Jun. 25, 2009

(65) Prior Publication Data
US 2010/0311926 A1    Dec. 9, 2010

Related U.S. Application Data

(60) Provisional application No. 61/125,330, filed on Apr. 23, 2008.

(30) Foreign Application Priority Data

Dec. 18, 2007   (EP) .................................... 07024481

(51) Int. Cl.
C08F 4/6592     (2006.01)
C08F 4/642      (2006.01)
(52) U.S. Cl. ........ 526/161; 526/160; 526/165; 526/943; 502/103; 502/155; 556/53
(58) Field of Classification Search .................... 556/53, 556/56; 502/103, 155; 526/160, 165, 161, 526/943
See application file for complete search history.

(56) References Cited

U.S. PATENT DOCUMENTS

| 5,646,083 A * | 7/1997 | van Beek ...................... 502/104 |
| 5,770,753 A | 6/1998 | Küber et al. |
| 5,942,459 A | 8/1999 | Sugano et al. |
| 6,087,291 A | 7/2000 | Speca et al. |
| 6,417,302 B1 | 7/2002 | Bohnen |
| 6,444,606 B1 | 9/2002 | Bingel et al. |
| 6,492,539 B1 * | 12/2002 | Bingel et al. .................... 556/11 |
| 6,589,905 B1 | 7/2003 | Fischer et al. |
| 6,620,953 B1 | 9/2003 | Bingel et al. |
| 7,342,078 B2 | 3/2008 | Schottek et al. |
| 2003/0036612 A1* | 2/2003 | Nifant'ev et al. ............. 526/160 |

FOREIGN PATENT DOCUMENTS

WO    WO 91/09882    7/1991

OTHER PUBLICATIONS

Erker, G. et al., "A Fulvene Route to Group 4 Metallocene Complexes Bearing 4,7-Bis(dimethylamino)-Substituted Indenyl Ligands," *Eur J. Inorg. Chem*, 2004, 11, 2260-2265.
Buchwald, G. et al., "A Simple Catalytic Method for the Conversion of Aryl Bromides to Arylamines," Ang. Chem. Int. Ed. Engl., 1995, 34, 12, 1348-1350.
Louie, J. and Hartwig, J.F., "Palladium-Catalyzed Synthesis of Arylamines from Aryl Halides. Mechanistic Studies Lead to Coupling in the Absence of Tin Reagents," *Tetrahedron Letters*, 1995, 36, No. 21, 3609-3612.
Benoit, H. Rempp, P. & Grubisic, Z., "A Universal Calibration for Gel Permeation Chromatography," *Journal of Polymer Sci., Phys. Ed.*, 1967, 5, 753-759.

* cited by examiner

*Primary Examiner* — Caixia Lu
(74) *Attorney, Agent, or Firm* — Dilworth IP LLC

(57) ABSTRACT

The present invention relates to a process for preparing transition metal compounds, in particular ansa-bisindenyl-metallocenes having nitrogen, phosphor, sulfur or oxygen comprising substituents, the corresponding transition metal compounds themselves and their use in the preparation of catalyst systems and also the use of the catalyst systems in the polymerization and copolymerization of olefins.

4 Claims, No Drawings

PROCESS FOR PREPARING TRANSITION METAL COMPOUNDS FOR OLEFINS POLYMERIZATION

This application claims priority to European Patent Application 07024481.9 filed 18 Dec. 2007 and provisional U.S. Appl. No. 61/125,330 filed 23 Apr. 2008; the disclosures of European Application 07024481.9 and U.S. application Ser. No. 61/125,330, each as filed, are incorporated herein by reference.

The present invention relates to a process for preparing transition metal compounds, in particular ansa-bisindenyl-metallocenes having special substituents, the corresponding transition metal compounds themselves and their use in the preparation of catalyst systems and also the use of the catalyst systems in the polymerization and copolymerization of olefins.

STATE OF THE ART

Research and development on preparation and use of organic transition metal compounds, in particular metallocenes, as catalyst components for the polymerization and copolymerization of olefins with the objective of preparing polyolefins has been pursued intensively at universities and in industry over the past 15 years.

EP 0 576 970 A1 for example describes $C_2$-symmetric metallocenes having aryl-substituted indenyl derivatives as ligands, the process for preparing them and their use as catalysts. According to this patent application, the metallocene catalysts are formed via a 2-alkyl-4-aryl-1-indanone as intermediate.

WO 01/48034 A2 describes ansa-bisindenyl-metallocenes having a combination of different substituents in positions 2 and 4 of the indenyl ligands. The catalyst systems obtained therefrom enable both propylene-ethylene copolymers as rubber phase with a sufficient molar mass and also propylene homopolymers having a sufficiently high melting point for satisfactory stiffness of the matrix to be produced.

So far, little data are available about heteroalkyl substituted metallocenes and their use in polymerization of olefins. Erker, G. et al. in Eur. J. Inorg. Chem. 2004, 11, 2260-2265 describes the synthesis of two metallocenes bearing 4,7-bis-dimethylamino-indene moiety. The 4,7-bis-dimethylamino-indene moiety is obtained via a two steps sequence in an overall yield of 81%. This elegant methodology allows access, on one hand, to only bis-amino indenes and on the other hand is neither versatile nor orthogonal.

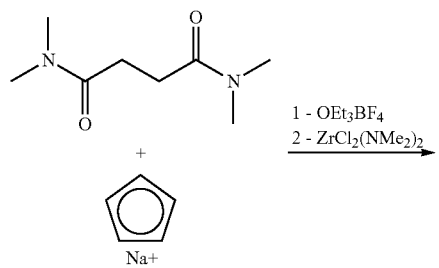

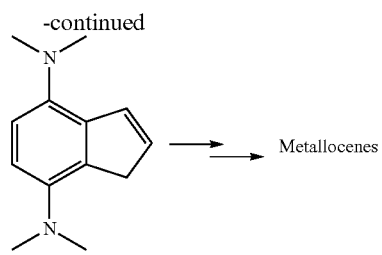

No data about polymerization of the produced metallocenes behaviour are disclosed.

In EP 0 728 773 A1 a metallocene bearing an indolyl moiety is described. The synthesis efficiency of the C—N bond formation is fairly low, about 17% yield.

Buchwald, S. L. et al. in Ang. Chem. Int. Ed. Engl. 1995, 34, 12, 1348-50 and Louie, J. and Hartwig, J. F. in Tetrahedron Letters, 1995, 36, No. 21, 3609, describe, independently, a new cross coupling reaction catalysed by palladium salts between primary/secondary amines and aromatic halogenids which give access with high efficiency to new C—N bonds.

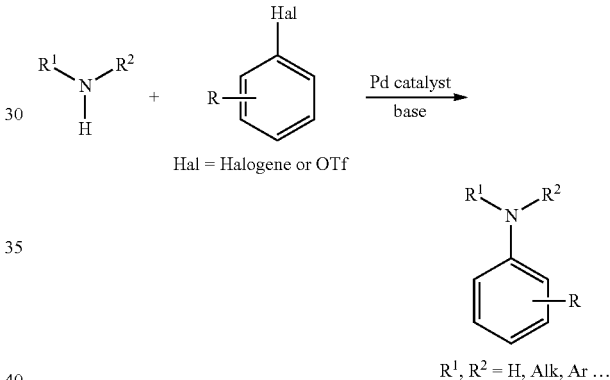

DETAILED DESCRIPTION OF THE INVENTION

It is an object of the invention to find novel metallocenes as catalysts or catalyst constituents for olefin polymerization obtainable by a simple method of preparation in high yields which are suitable for the preparation of polyolefins giving an opportunity to development of new polymers.

We have found that this object is achieved by the transition metal compounds as set forth in claim 1, a process for preparing these transition metal compounds as set forth in the independent process claim and their use as catalyst constituent in the (co)polymerization of olefins as set forth in the independent use claim.

Preferred embodiments are defined by the respective dependent claims.

Transition Metal Compounds

We have found a synthetic route by means of which it is possible to prepare novel metallocenes which have specific substituents, selected ansa-bisindenyl-metallocenes comprising at least one indenyl ligand which bears substituents being amine, phosphine, ether or thioether in position 4 and/or 5.

In a first aspect, the present invention accordingly provides transition metal compounds of the formula (I)

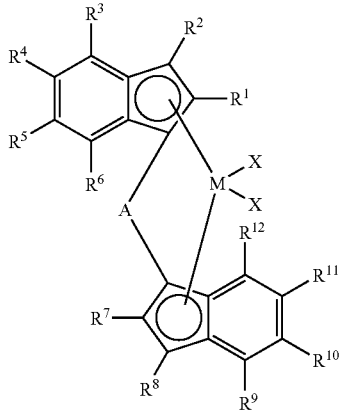

where
M is a metal of group IV of the Periodic Table,
$R^3$, $R^4$, $R^9$, and $R^{13}$ are identical or different and
are each selected from hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $G^1(R^{13}R^{14})$ and $G^2(R^{13})$, wherein at least one of $R^3$ and $R^4$ is selected from $G^1(R^{13}R^{14})$ and $G^2(R^{13})$,
$G^1$ is N or P and
$G^2$ is S or O,
$R^1$, $R^2$, $R^5$, $R^6$, $R^7$, $R^8$, $R^{11}$, $R^{12}$
are identical or different and are each hydrogen, $C_1$-$C_{10}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part,
wherein $R^4$ and $R^5$ together with the carbon atoms connecting them may also form a saturated or unsaturated ring system having from 4 to 15 carbon atoms,
wherein $R^{10}$ and $R^{11}$ together with the carbon atoms connecting them may also form a saturated or unsaturated ring system having from 4 to 15 carbon atoms,
$R^{13}$, $R^{14}$
are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part and may also contain heteroatoms selected from the group consisting of the elements N, P, O, S, Si, or
together may form a aromatic or aliphatic heterocycle having from 4 to 20 carbon atoms in the ring which may bear a substituent selected from $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part wherein the substituent may also contain heteroatoms selected from the group consisting of the elements N, P, O, S, Si, X is halogen, a $C_1$-$C_{20}$-alkyl or a $C_6$-$C_{15}$-aryl, A represents two substituents as defined for $R^1$ or is a bridge selected

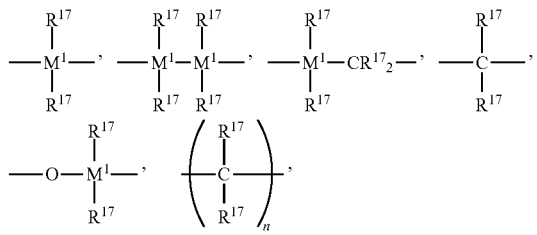

$=BR^{17}$, $=AlR^{17}$, —Ge—, —Sn—, —O—, —S—, $=SO$, $=SO_2$, $=NR^{17}$, —CO, $=PR^{17}$ or $=P(O)R^{17}$, where
$R^{17}$ are identical or different and are each hydrogen, halogen, $C_1$-$C_{10}$-alkyl, $C_1$-$C_{10}$-fluoroalkyl, $C_6$-$C_{10}$-fluoroaryl, $C_6$-$C_{10}$-aryl, $C_1$-$C_{10}$-alkoxy, $C_2$-$C_{10}$-alkenyl, $C_7$-$C_{40}$-arylalkyl, $C_8$-$C_{40}$-arylalkenyl, $C_7$-$C_{40}$-alkylaryl or two radicals $R^{17}$ together with the atoms connecting them form a ring,
n is an integer from 2 to 6, and
$M^1$ is silicon, germanium or tin.

Particular preference is given to compounds of the formula (I) in which
M is zirconium,
$R^3$, $R^4$, $R^9$, $R^{10}$ are independently
selected from hydrogen, $C_1$-$C_8$-alkyl, or two adjacent radicals together with the atoms connecting them form a saturated or unsaturated ring system having from 4 to 15 carbon atoms, $N(R^{13}R^{14})$,
wherein at least one of $R^3$ and $R^4$ is $N(R^{13}R^{14})$,
$R^{13}$, $R^{14}$ are identical or different and are each $C_1$-$C_{20}$-alkyl, $C_6$-$C_{15}$-aryl or alkylaryl having from 1 to 10 carbon atoms in the alkyl part and from 6 to 20 carbon atoms in the aryl part,
$R^5$, $R^6$, $R^{11}$, $R^{12}$ are identical or different and
are each selected from hydrogen, $C_1$-$C_8$-alkyl, 3- to 8-membered cycloalkyl which may in turn bear a $C_1$-$C_8$-alkyl group as substituent, $C_6$-$C_{15}$-aryl, alkylaryl having from 1 to 10 carbon atoms in the alkyl part and from 6 to 20 carbon atoms in the aryl part,
wherein $R^4$ and $R^5$ together with the carbon atoms connecting them may also form a saturated or unsaturated ring system having from 4 to 15 carbon atoms, and
wherein $R^{19}$ and $R^{11}$ together with the carbon atoms connecting them may also form a saturated or unsaturated ring system having from 4 to 15 carbon atoms,
$R^2$, $R^8$ are each hydrogen,
$R^1$, $R^7$ are identical or different and identical or different and are each hydrogen, $C_1$-$C_{12}$-alkyl group,
X is halogen or a $C_1$-$C_8$-alkyl,
A is a bridge selected from —$CH_2$—, —$C_2H_4$—, —$Si(CH_3)_2$—, —$C_3H_6$—, —$C(CH_3)_2$—.

Very Particular Preference is Given to Metallocenes of the Formula (I)
in which $R^1$ and $R^7$ are the same or different and each $C_{1-8}$-alkyl, preferably methyl, ethyl, n-propyl, isopropyl, n-butyl, isobutyl, sec-butyl, tert-butyl, cyclopentyl or cyclohexyl, particularly preferably methyl, ethyl or isopropyl, $R^2$, $R^6$, $R^8$ and $R^{12}$ are each hydrogen and, $R^3$ is $N(R^{13}R^{14})$ and $R^9$ is $N(R^{13}R^{14})$ or $C_6$-$C_{20}$-aryl and $R^4$, $R^5$, $R^{10}$, $R^{11}$ are each hydrogen or $R^4$ and $R^5$ as well as $R^{19}$ and $R^{11}$ together with the carbon atoms connecting them form a cyclopentane ring and thus together with the indenyl an indacenyl ring system Nonlimiting examples of very particularly preferred transition metal compounds of the formula (I) are:
rac dimethylsilyl bis[2-methyl-4-(N-methyl phenylamino) indenyl]zirconium dichloride, rac dimethylsilyl bis(2-methyl 4-N,N-diphenylamino indenyl)zirconium dichloride, rac dimethylsilyl bis(4-N-methyl phenylamino indacenyl)-zirconiumdichloride, rac dimethylsilyl (2-methyl-4-(N-methyl phenylamino indenyl)(2-methyl 4-N,N-diphenylamino indenyl)zirconium dichloride, rac dimethylsilyl (2-methyl-4-(N-methyl phenylamino indenyl)(2-methyl-4-phenylindenyl)zirconium dichloride, rac dimethylsilyl [2-methyl-4-(N-methyl phenylamino) indenyl][2-methyl-5-(N-methyl phenylamino)indenyl]zirconium dichloride.

Preference is also given to the corresponding dimethylzirconium compounds, the corresponding $\eta^4$-butadiene zirconium compounds and metallocenes of the formula (I) having zirconium fragments as described in WO 00/31090 A1, and also the corresponding titanium and hafnium compounds.

The present invention further provides a ligand system of the formula (II) or its double bond isomers,

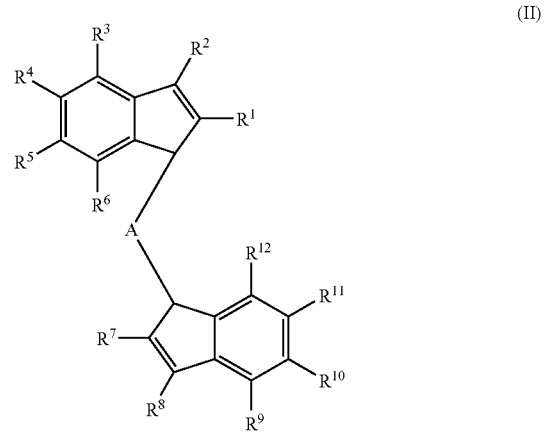

where the variables are as defined for formula (I), including the preferred embodiments.

Process

We have found a synthetic route by means of which it is possible to prepare indenyl metallocenes having special substituents.

The synthesis of the metallocenes of the present invention is in principle carried out according to the following simplified scheme:

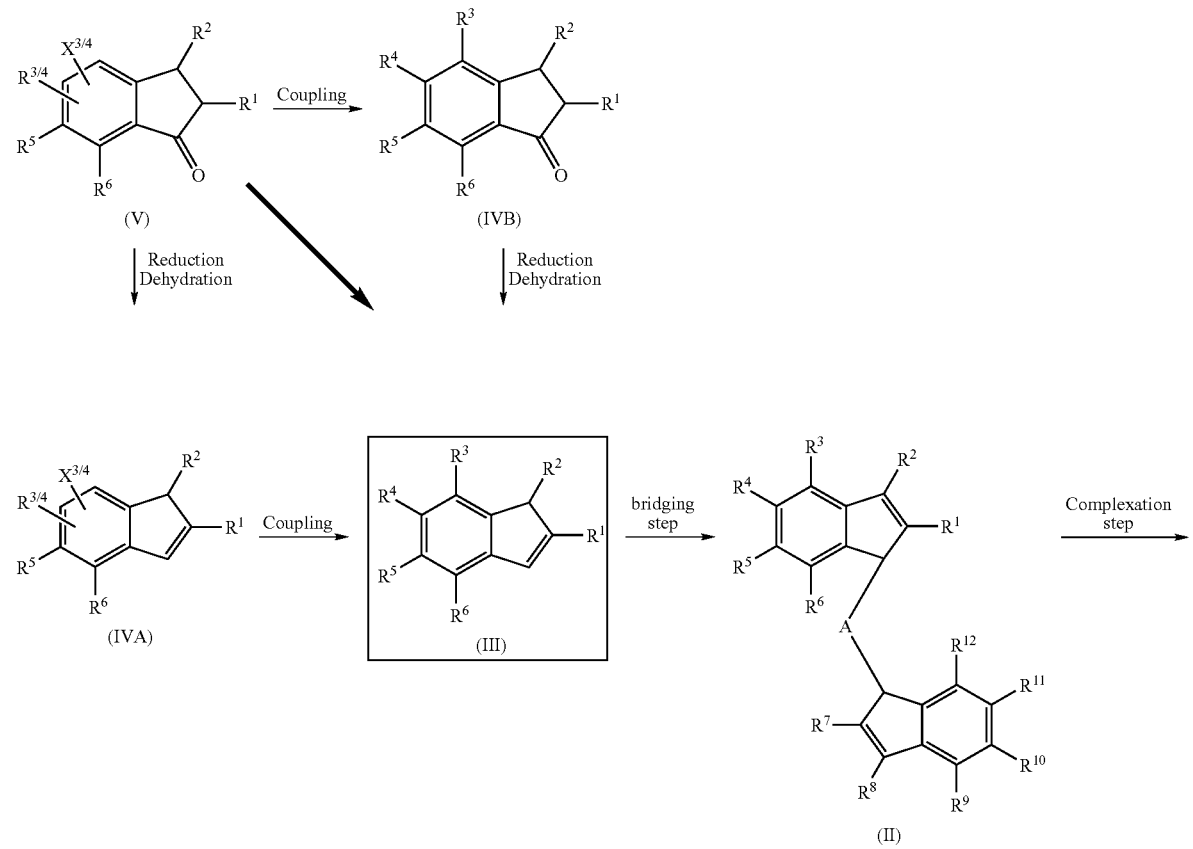

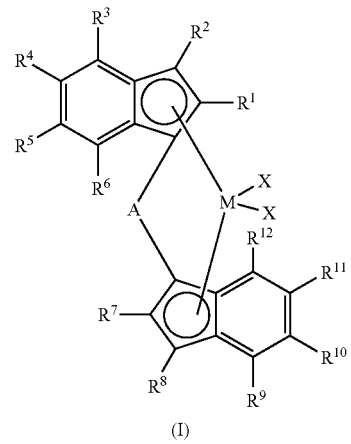

(I)

The present invention thus also provides a process for preparing ansa-metallocenes of the formula (I) which comprises the following steps:

a) reaction of a 1-indanone of the formula (V) with a compound $HR^3$ and/or $HR^4$ and prior or subsequent reduction/elimination to form the substituted indene of the formula (III), where the variables $R^3$ and $R^4$ are independently selected from $G^1(R^{13}R^{14})$ and $G^2(R^{13})$ and $G^1, G^2, R^{13}$ and $R^{14}$ are as defined for formula (I), b) optional deprotonation of the substituted indene of the formula (III) and subsequent reaction of the deprotonated indene with a bridging compound of the type $AZ_2$, where Z is Cl, Br, I or O-tosyl and A is as defined for formula (I) and reaction of the thus formed compound with a further deprotonated indene to form the ligand system of the formula (IIa) or its double bond isomers,

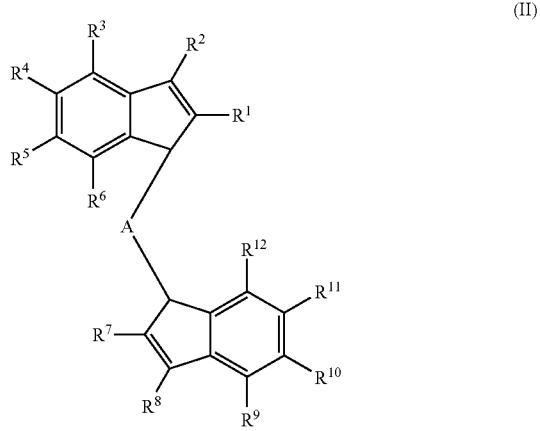

(II)

c) deprotonation of the ligand system of the formula (II) or its double bond isomers and reaction with compounds of the type $Y_2MX_2$ to give the ansa-metallocene of the formula (I), where Y is a halogene or O-tosyl and M and X are as defined for formula (I).

The substituted 1-indanones of the formula are obtainable in a simple manner by synthetic methods known from the prior art, for example the process described in WO 98/40331.

Reaction of a 1-indanone of the formula (V) with a compound $HR^3$ and/or $HR^4$ and prior or subsequent reduction-elimination to form the substituted indene of the formula (III) means a) reaction of a 1-indanone of the formula (Va)

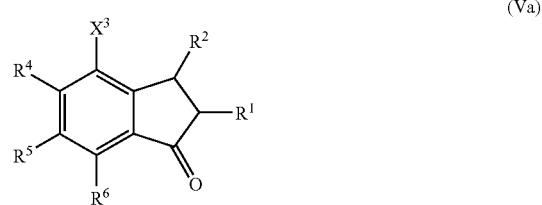

(Va)

with a compound $HR^3$ wherein $R^3$ is selected from $G^1(R^{13}R^{14})$ and $G^2(R^{13})$, $X^3$ is selected from Cl, Br, I or O-Tf (trifluoro methane sulfonyl), $R^4$ is selected from hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $G^1$ is N or P and $G^2$ is S or O, $R^1, R^2, R^5, R^6$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, wherein $R^4$ and $R^5$ together with the carbon atoms connecting them may also form a saturated or unsaturated ring system having from 4 to 15 carbon atoms, $R^{13}, R^{14}$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part and may also contain heteroatoms selected from the group consisting of the elements N, P, O, S, Si, or together may form a aromatic or aliphatic heterocycle having from 4 to 20 carbon atoms in the ring which may bear a substituent selected from $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part wherein the substituent may also contain heteroatoms selected from the group consisting of the elements N, P, O, S, Si, Or b) reaction of a 1-indanone of the formula (Vb)

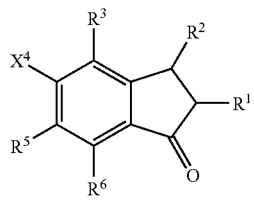

(Vb)

with a compound $HR^4$ wherein $R^4$ is selected from $G^1(R^{13}R^{14})$ and $G^2$ ($R^{13}$), $X^4$ is selected from Cl, Br, I or O-Tf, $R^3$ is selected from hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $G^1$ is N or P and $G^2$ is S or O, $R^1$, $R^2$, $R^5$, $R^6$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $R^{13}$, $R^{14}$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part and may also contain heteroatoms selected from the group consisting of the elements N, P, O, S, Si, or together may form a aromatic or aliphatic heterocycle having from 4 to 20 carbon atoms in the ring which may bear a substituent selected from $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part wherein the substituent may also contain heteroatoms selected from the group consisting of the elements N, P, O, S, Si, Or c) reaction of a 1-indanone of the formula (Vc)

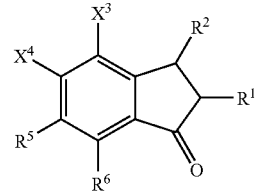

(Vc)

with a compound $HR^3$ and $HR^4$ wherein $R^3$ and $R^4$ are the same or different and are selected from $G^1(R^{13}R^{14})$ and $G^2$ ($R^{13}$), $X^3$ and $X^4$ are the same or different and are selected from Cl, Br, I or O-Tf, $G^1$ is N or P and $G^2$ is S or O, $R^1$, $R^2$, $R^5$, $R^6$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $R^{13}$, $R^{14}$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part and may also contain heteroatoms selected from the group consisting of the elements N, P, O, S, Si, or together may form a aromatic or aliphatic heterocycle having from 4 to 20 carbon atoms in the ring which may bear a substituent selected from $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part wherein the substituent may also contain heteroatoms selected from the group consisting of the elements N, P, O, S, Si.

Especially preferred is a process which comprises the reaction of a 1-indanone of the formula (Va)

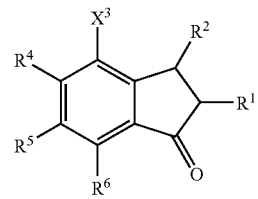

(Va)

with a compound $HR^3$ wherein $R^3$ is $G^1(R^{13}R^{14})$, $X^3$ is selected from Cl, Br, I or O-Tf, $R^4$ is selected from hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $G^1$ is N and $R^1, R^2, R^5, R^6$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $R^{13}, R^{14}$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part and may also contain heteroatoms selected from the group consisting of the elements N, P, O, S, Si, or together may form an aromatic or aliphatic heterocycle having from 4 to 20 carbon atoms in the ring which may bear a substituent selected from $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part wherein the substituent may also contain heteroatoms selected from the group consisting of the elements N, P, O, S, Si, wherein $R^4$ and $R^5$ together with the carbon atoms connecting them may also form a saturated or unsaturated ring system having from 4 to 15 carbon atoms.

The reaction of indanone with the compound $HR^3$ and/or $HR^4$ is preferably performed in presence of a palladium catalyst and a strong base in an inert solvent at 20° C. to 200° C.

For the process according to the invention, the palladium catalyst preferably contains at least one phosphorus-containing ligand.

The palladium catalyst may already contain the at least one phosphorus-containing ligand, but the palladium catalyst containing the phosphorus-containing ligands can also be formed from catalyst precursors.

The term "palladium precursor" as used herein represents a palladium source capable of generating a catalytic system in combination with a suitable ligand and base.

The catalyst precursors used in this connection are preferably palladium(0) or -(II) compounds in the presence of phosphorus-containing ligands such as phosphine ligands.

Palladium compounds which can be used are Pd(0)-complex compounds and Pd(II) compounds. Suitable examples are palladium acetates, halides, nitrates, carbonates, ketonates, acetylacetonates, nitrilopalladium halides, olefinpalladium halides, allylpalladium halides and palladium biscarboxylates. Specific examples are $Pd(OAc)_2$, $Pd(acac)_2$, $(CH_3CN)_2$, $Pd(NO_2)Cl$, $(C_{10}H_8N_2)PdCl_2$, $Pd(dba)_2$, $Pd_2(dba)_3$ and $PdCl_2$.

Palladium precursors used with preference are palladium (II) acetate, didibenzylideneacetone palladium(0), trisdibenzylideneacetone palladium(0), allylpalladium(II) chloride dimer, palladium(II) chloride, palladium(II) acetylacetonate or palladium(II) nitrate. Particular preference is given to didibenzylideneacetonepalladium(0) and trisdibenzylideneacetonepalladium(0).

The palladium compound can also be produced in situ, for example from palladium(II) acetate or palladium(II) chloride by adding a customary reducing agent.

Preferred ligand(s) are mono- and bidentate phosphorus compounds. Examples of compounds which are suitable as phosphine ligands are triphenylphosphine, tricyclohexylphosphine, bisdiphenylphosphinoethane, bisdiphenylphosphinopropane, bisdiphenylphosphinobutane, tri-n-butylphosphine, tri-tert.-butylphosphine, triisopropylphosphine, bisdiphenylphosphinobenzene, bisdiphenylphosphinobinaphthyl, diphenylphosphinopyridine, it being possible for the phenyl radicals to be substituted or, when required, replaced by one or more $C_1$ to $C_{12}$-alkyl or $C_3$ to $C_{10}$-cycloalkyl groups. A particularly preferred ligand is tri-tert.-butylphosphine.

The ligands are used inter alia in a P/Pd ratio of 8:1 to 1:1. The catalyst is generally used in quantities of from 0.0001 mol-% to 10 mol-%, preferably from 0.001 mol-% to 5 mol-% (based on the haloaromatics).

In the process of the invention, amines react with chloroaromatics over a palladium catalyst in the presence of a strong base the pKa value of which is preferably higher than 10. Examples of bases which can be used are strongly basic alkali metal and alkaline earth metal derivatives such as alkali metal alkoxides and alkaline earth metal alkoxides, alkali metal and alkaline earth metal amides, and also butyllithium, phenyllithium, etc. Preferred bases are alkali metal and alkaline earth metal alkoxides such as sodium tert-butoxide, potassium tert-butoxide, lithium tert-butoxide, sodium phenoxide, potassium phenoxide and potassium carbonate, sodium hexamethyldisilazide and lithium hexamethyldisilazide.

The base(s) used are preferably alkali metal or alkaline earth metal phosphates, for example potassium phosphate, alkali metal or alkaline earth metal carbonates, for example caesium carbonate, alkali metal or alkaline earth metal hydroxides, for example sodium hydroxide or potassium hydroxide, or alkali metal alkoxides or alkaline earth metal alkoxides. Preferred bases are alkali metal alkoxides or alkaline earth metal alkoxides, such as sodium tert. butoxide, potassium tert.-butoxide, lithium tert. butoxide, sodium phenoxide, sodium phenoxide, potassium phenoxide and potassium carbonate, sodium hexamethyldisilazide and lithium hexamethylsilazide.

The base is preferably used in a quantity of 0.5-5 equivalents, in particular 1-3 equivalents and very particularly preferably 1.2-2 equivalents, based on the haloaromatics.

The solvents used are usually inert organic solvents. Preference is given to aromatic hydrocarbons such as toluene, xylenes, anisole, tetralin and aliphatic ethers such as tetrahydrofuran, dimethoxyethane, dioxane, tetrahydropropane, DMSO, DMF and formaldehyde acetals.

The haloaromatics are reacted at temperatures of from 20° C. to 200° C., preferably at 40° C.-100° C. and particularly preferably at 60° C.-80° C.

The process according to the invention is particularly suitable for the reaction of secondary aliphatic amines. The amine is usually added in virtually stoichiometric quantities or in excess, based on the haloaromatics. The quantity of amine is preferably 1 to 3 equivalents, in particular 1.2 to 2 equivalents After or prior to the reaction with the suitable compound $HR^3$ and/or $HR^4$, a reduction-elimination reaction is carried out to form the double bond in the 5-membered ring. The reduction can be induced by a reduction agent, such as NaBH$_4$, LiAlH$_4$, or KBH$_4$ for transforming the indanone into the respective alcohol. The reduction also is possible by reaction with Al(iBu)$_3$, Al(iPr)$_3$. In some case hydrogenation with hydrogen in presence of a Raney-Ni-catalyst is possible. Elimination can, for example, be induced by means of a suitable dilute or undiluted acid, e.g. hydrochloric acid, sulfuric acid, phosphoric acid or an organic acid such as para-toluensulfonic acid, formic acid, acetic acid, citric acid and the like.

This gives a substituted indene of the formula (III) which optionally, after deprotonation on the methylene carbon of the 5-membered ring, is reacted with a reagent AZ$_2$, in the simplest case a dialkyldichlorosilane. The deprotonation is carried out using suitable bases such as n-butyllithium, tert-butyllithium, methyllithium, potassium hydride, dibutylmagnesium or the like. Appropriate process steps are known from the prior art and are described, for example, in WO 01/48034 A2.

These reaction products may be subsequently reacted with a deprotonated indene to form the corresponding ligand system (II).

The ligands (II) obtained in this way are in turn converted by deprotonation and subsequent reaction with compounds of the type Y$_2$MX$_2$ into the corresponding C$_1$—, C$_2$ or Cs-symmetric ansa-metallocenes of the formula (I). The procedures for synthesizing the complexes are known standard methods of the prior art.

Indenes

The present invention also provides indenes of the formula (III) or the double bond isomers thereof

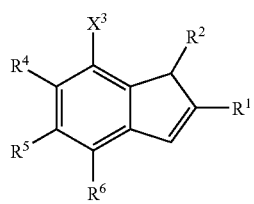
(III)

where the variables R$^1$, R$^2$, R$^3$, R$^4$, R$^5$ and R$^6$ are as defined for formula I.

The novel metallocenes of the formula (I) are particularly suitable as constituents of catalyst systems for preparing polyolefins by polymerization of at least one olefin in the presence of a catalyst comprising at least one cocatalyst and at least one metallocene.

Preference is given to using the racemic or pseudo-racemic metallocenes of the formula (I), but the use of racemic or pseudo-rac-enriched (pseudo-)rac/(pseudo-) meso mixtures can also be appropriate.

Catalyst Systems

The present invention therefore also provides a catalyst system comprising at least one metallocene of the formula (I) (component A)) as organometallic transition metal compound and at least one cocatalyst (component B)).

Together with the novel metallocene of the formula (I), the cocatalyst forms a polymerization-active catalyst system in which the cocatalyst serves as cation-forming compound.

Suitable cation-forming compounds (components B)) which are able to react with a novel organometallic transition metal compound to convert it into a cationic compound are, for example, compounds such as an aluminoxane, a strong uncharged Lewis acid, an ionic compound having a Lewis-acid cation or an ionic compound containing a Brönsted acid as cation. In the case of metallocene complexes as organometallic transition metal compound, the cation-forming compounds are frequently also referred to as compounds capable of forming metallocenium ions.

As aluminoxanes, it is possible to use, for example, the compounds described in WO 00/31090 A1. Particularly useful compounds are open-chain or cyclic aluminoxane compounds of the formula (VI) or (VII)

(VI)

(VII)

where

R$^{21}$ is a C$_1$-C$_4$-alkyl group, preferably a methyl or ethyl group, and m is an integer from 5 to 30, preferably from 10 to 25.

These oligomeric aluminoxane compounds are usually prepared by reacting a solution of trialkylaluminum with water. The oligomeric aluminoxane compounds obtained in this way are generally in the form of mixtures of both linear and cyclic chain molecules of various lengths, so that m is to be regarded as a mean. The aluminoxane compounds can also be present in admixture with other metal alkyls, preferably aluminum alkyls.

In place of the aluminoxane compounds of the formulae (VI) or (VII), modified aluminoxanes in which some of the hydrocarbon radicals or hydrogen atoms are replaced by alkoxy, aryloxy, siloxy or amide groups can also be used as component B).

It has been found to be advantageous to use the novel organometallic transition metal compound and the aluminoxane compounds in such amounts that the atomic ratio of aluminum from the aluminoxane compounds to the transition metal from the organometallic transition metal compound is in the range from 10:1 to 1000:1, preferably from 20:1 to 500:1 and in particular in the range from 30:1 to 400:1.

As strong, uncharged Lewis acids, preference is given to compounds of the formula (VIII)

M$^4$X$^1$X$^2$X$^3$ (VIII)

where

M$^4$ is an element of group 13 of the Periodic Table of the Elements, in particular B, Al or Ga, preferably B, X$^1$, X$^2$ and X$^3$ are each hydrogen, C$_1$-C$_{10}$-alkyl, C$_6$-C$_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are given in WO 00/31090.

Particular preference is given to compounds of the formula (VIII) in which X$^1$, X$^2$ and X$^3$ are identical, preferably tris(pentafluorophenyl)borane.

Further strong uncharged Lewis acids suitable as cation-forming compounds B) are the reaction products from the reaction of a boronic acid with two equivalents of a trialkylaluminum or the reaction products from the reaction of a trialkylaluminum with two equivalents of an acidic fluorinated, in particular perfluorinated, hydrocarbon compound such as pentafluorophenol or bis(pentafluorophenyl)borinic acid.

Suitable ionic compounds having Lewis-acid cations are salt-like compounds of the cation of the formula (IX)

$$[(Y^{a+})Q_1Q_2\ldots Q_z]^{d+} \qquad (IX)$$

where

Y is an element of groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may be substituted by $C_1$-$C_{10}$-alkyl groups, halogen, $C_1$-$C_{28}$-alkoxy, $C_6$-$C_{15}$-aryloxy, silyl or mercapto groups, a is an integer from 1 to 6 and z is an integer from 0 to 5, d corresponds to the difference a-z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are mentioned in WO 91/09882 A1, preferably tetrakis(pentafluorophenyl)borate.

Salts containing noncoordinating anions can also be prepared by combining a boron or aluminum compound, e.g. an aluminum alkyl, with a second compound which can react to link two or more boron or aluminum atoms, e.g. water, and a third compound which reacts with the boron or aluminum compound to form an ionizing ionic compound, e.g. triphenylchloromethane. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acids, particular preference is given to protonated amine or aniline derivatives. Preferred cations are N,N-dimethylanilinium, N,N-dimethylcyclohexylammonium and N,N-dimethylbenzylammonium and also derivatives of the latter two.

Preferred ionic compounds B) are, in particular, N,N-dimethylanilinium tetrakis(pentafluorophenyl)borate, N,N-dimethylcyclohexylammonium tetrakis(pentafluoro-phenyl)borate or N,N-dimethylbenzylammonium tetrakis(pentafluorophenyl)borate.

Two or more borate anions can also be joined to one another, as in the dianion $[(C_6F_5)_2B-C_6F_4-B(C_6F_5)_2]^{2-}$, or the borate anion can be bound via a bridge having a suitable functional group to a support surface.

Further suitable cation-forming compounds B) are listed in WO 00/31090 A1.

The amount of strong, uncharged Lewis acids, ionic compounds having Lewis-acid cations or ionic compounds containing Brönsted acids as cations is preferably from 0.1 to 20 equivalents, preferably from 1 to 10 equivalents, based on the organometallic transition metal compound of the present invention.

Further suitable cation-forming compounds B) are boron-aluminum compounds such as di[bis(pentafluorophenyl-boroxy)]methylalane. Such boron-aluminum compounds are disclosed, for example, in WO 99/06414 A1.

It is also possible to use mixtures of all the abovementioned cation-forming compounds B). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Preference is given to using both the novel organometallic transition metal compound and the cation-forming compounds B) in a solvent, with aromatic hydrocarbons having from 6 to 20 carbon atoms, in particular xylene and toluene, being preferred.

The catalyst may further comprise, as additional component C), a metal compound of the formula (X), $$M^5(R^{22})_r(R^{23})_s(R^{24})_t \qquad (X)$$

where $M^5$ is an alkali metal, an alkaline earth metal or a metal of group 13 of the Periodic Table, i.e. boron, aluminum, gallium, indium or thallium, $R^{22}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{23}$ and $R^{24}$ are each hydrogen, halogen, $C_1$-$C_{10}$-alkyl, $C_6$-$C_{15}$-aryl, alkylaryl, arylalkyl or alkoxy each having from 1 to 10 carbon atoms in the alkyl radical and from 6 to 20 carbon atoms in the aryl radical, r is an integer from 1 to 3 and s and t are integers from 0 to 2, where the sum r+s+t corresponds to the valence of $M^5$, with the component C) not being identical to the component B). It is also possible to use mixtures of various metal compounds of the formula (X).

Among the metal compounds of the formula (X), preference is given to those in which $M^5$ is lithium, magnesium or aluminum and $R^{23}$ and $R^{24}$ are each $C_1$-$C_{10}$-alkyl.

Particularly preferred metal compounds of the formula (X) are n-butyllithium, n-butyl-n-octylmagnesium, n-butyl-n-heptylmagnesium, tri-n-hexylaluminum, triisobutylaluminum, triethylaluminum and trimethylaluminum and mixtures thereof.

If a metal compound is used as component C), it is preferably present in the catalyst in such an amount that the molar ratio of $M^5$ from formula (X) to transition metal $M^1$ from the organometallic transition metal compound of the present invention is from 800:1 to 1:1, in particular from 200:1 to 2:1.

Particular preference is given to a catalyst system comprising an organometallic transition metal compound according to the present invention (component A)) and at least one cocatalyst (component B)) and, in addition, a support (component D)).

To obtain such a supported catalyst system, the unsupported catalyst system can be reacted with a support (component D)). The order in which component D), the organometallic transition metal compound of the present invention and the cocatalyst are combined is in principle immaterial. The organometallic transition metal compound and the cocatalyst can be fixed to the supports either independently of one another or simultaneously. After the individual process steps, the solid can be washed with suitable inert solvents such as aliphatic or aromatic hydrocarbons.

As component D), preference is given to using finely divided supports which can be any organic or inorganic, inert solids. In particular, the component D) can be a porous support such as talc, a sheet silicate, an inorganic oxide or a finely divided polymer powder (e.g. polyolefin).

Suitable inorganic oxides may be found among oxides of the elements of groups 2, 3, 4, 5, 13, 14, 15 and 16 of the Periodic Table of the Elements. Examples of oxides preferred as supports include silicon dioxide, aluminum oxide and also mixed oxides of the elements calcium, aluminum, silicon, magnesium and titanium and also corresponding oxide mixtures. Other inorganic oxides which can be used alone or in combination with the abovementioned preferred oxidic supports are, for example, MgO, $ZrO_2$, $TiO_2$ or $B_2O_3$. A preferred mixed oxide is, for example, calcined hydrocalcite.

The support materials used preferably have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 100 μm.

The inorganic support can be subjected to a thermal treatment, e.g. for the removal of adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1000° C. to set, if appropriate, the desired structure of the solid and/or the desired OH concentration on the surface. The support can also be treated chemically using customary desiccants such as metal alkyls, preferably aluminum alkyls, chlorosilanes or $SiCl_4$, or else methylaluminoxane. Such treatment methods are described, for example, in WO 00/31090 A1.

The inorganic support material can also be modified chemically. For example, the treatment of silica gel with $NH_4SiF_6$ leads to fluorination of the silica gel surface and the treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and should preferably likewise be freed of adhering moisture, solvent residues or other impurities by appropriate purification and drying operations before use. It is also possible to use functionalized polymer supports, e.g. ones based on polystyrenes, via whose functional groups, for example ammonium or hydroxy groups, at least one of the catalyst components can be immobilized.

In a preferred method of preparing the supported catalyst system, at least one of the organometallic transition metal compounds of the present invention is brought into contact with at least one cocatalyst component B) in a suitable solvent, preferably giving a soluble reaction product, an adduct or a mixture.

The preparation obtained in this way is then mixed with the dehydrated or passivated support material, the solvent is removed and the resulting supported organometallic transition metal compound catalyst system is dried to ensure that all or most of the solvent is removed from the pores of the support material. The supported catalyst is obtained as a free-flowing powder. Examples of the industrial implementation of the above process are described in WO 96/00243 A1, WO 98/40419 A1 or WO 00/05277 A1.

A further preferred embodiment comprises firstly applying the cation-forming compound to the support component and subsequently bringing this supported cation-forming compound into contact with the organometallic transition metal compound of the present invention.

Thus, useful cocatalyst systems B) likewise include combinations which are obtained by combining the following components:
1. at least one defined boron or aluminum compound,
2. at least one uncharged compound which has at least one acidic hydrogen atom,
3. at least one support, preferably an inorganic oxidic support, and optionally a base, preferably an organic nitrogen-containing base such as an amine, an aniline derivative or a nitrogen heterocycle.

The boron or aluminum compounds used in the preparation of the supported cocatalysts are preferably compounds of the formula XI

(XI)

where
$R^{70}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, or $R^{70}$ is an $OSiR^{77}_3$ group, where
$R^{77}$ are identical or different and are each hydrogen, halogen, $C_1$-$C_{20}$-alkyl, $C_1$-$C_{20}$-haloalkyl, $C_1$-$C_{10}$-alkoxy, $C_5$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_{10}$-alkyl or $C_7$-$C_{20}$-arylalkyl, and
$M^6$ is boron or aluminum, preferably aluminum.

Particularly preferred compounds of the formula XI are trimethylaluminum, triethylaluminum and triisobutylaluminum.

The uncharged compounds which have at least one acidic hydrogen atom and can react with compounds of the formula (XI) are preferably compounds of the formulae XII, XIII or XIV,

(XII)

(XIII)

(XIV)

where
$R^{71}$ are identical or different and are each hydrogen, halogen, a boron-free $C_1$-$C_{40}$ group such as $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, an $Si(R^{73})_3$ group or a $CH(SiR^{73}_3)_2$ group, where
$R^{73}$ is a boron-free $C_1$-$C_{40}$ group such as $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, and
$R^{72}$ is a divalent $C_1$-$C_{40}$ group such as $C_1$-$C_{20}$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene,
D is an element of group 16 of the Periodic Table of the Elements or an $NR^{74}$ group, where $R^{74}$ is hydrogen or a $C_1$-$C_{20}$-hydrocarbon radical such as $C_1$-$C_{20}$-alkyl or $C_6$-$C_{20}$-aryl, preferably oxygen, and
h is 1 or 2.

Suitable compounds of the formula (XII) are water, alcohols, phenol derivatives, thiophenol derivatives or aniline derivatives, with the halogenated and in particular the perfluorinated alkyls and phenols being of special significance. Examples of particularly useful compounds are pentafluorophenol, 1,1-bis(pentafluorophenyl)methanol and 4-hydroxy-2,2',3,3',4,4',5,5',6,6'-nonafluorobiphenyl.

Suitable compounds of the formula (XIII) are boronic acids and borinic acids, in particular borinic acids having perfluorinated aryl radicals, for example $(C_6F_5)_2BOH$. Suitable compounds of the formula (XIV) are dihydroxy compounds in which the divalent carbon-containing group is preferably halogenated, in particular perfluorinated. An example of such a compound is 4,4'-dihydroxy-2,2',3,3',5,5',6,6'-octafluorobiphenyl hydrate.

Examples of combinations of compounds of the formula (XI) with compounds of the formula (XII) or (XIV) are trimethylaluminum/pentafluorophenol, trimethylaluminum/1-bis(pentafluorophenol)methanol, trimethylaluminum/4-hydroxy-2,2',3,3',4,4',5,5',6,6'-nonafluorobiphenyl, triethylaluminum/pentafluorophenol, triisobutylaluminum/pentafluorophenol and triethylaluminum/4,4'-dihydroxy-2,2',3,3',5,5',6,6'-octafluorobiphenyl hydrate, with, for example, reaction products of the following types being able to be formed.

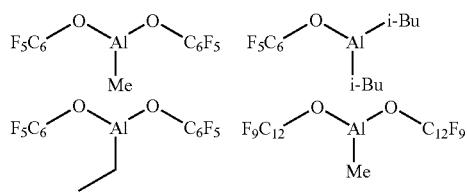

Examples of reaction products from the reaction of at least one compound of the formula (XI) with at least one compound of the formula (XIII) are:

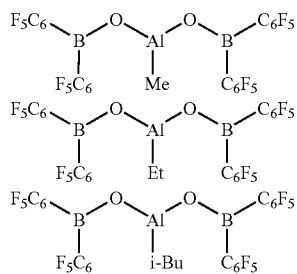

In principle, the components can be combined in any way.

The reaction products from the reaction of at least one compound of the formula XI with at least one compound of the formula XII, XIII or XIV and optionally the organic nitrogen base may additionally be combined with an organometallic compound of the formula VI, VII, VIII and/or X so as then to form, together with the support, the supported cocatalyst system B).

In a preferred embodiment, the components 1 (formula XI) and 2 (formula XII, XIII or XIV) and the components 3 (support) and 4 (base) are combined separately and subsequently reacted with one another, with the reaction preferably taking place in an inert solvent or suspension medium. The supported cocatalyst B) formed can be freed of the inert solvent or suspension medium before it is reacted with the organometallic transition metal component of the present invention and any component C) to form the catalyst system.

It is also possible firstly to prepolymerize the catalyst solid with α-olefins, preferably linear $C_2$-$C_{10}$-1-alkenes and in particular ethylene or propylene, and then to employ the resulting prepolymerized catalyst solid in the actual polymerization. The mass ratio of catalyst solid used in the prepolymerization to polymerized-on monomer is usually in the range from 1:0.1 to 1:200.

Furthermore, a small amount of an olefin, preferably an α-olefin, for example vinylcyclohexane, styrene or phenyldimethylvinylsilane, as modified component, an antistatic or a suitable inert compound such as a wax or oil can be added as additive during or after the preparation of the supported catalyst system. The molar ratio of additives to the organometallic transition metal compound of the present invention is usually from 1:1000 to 1000:1, preferably from 1:5 to 20:1.

Polymerization Process

The present invention also provides a process for preparing polyolefins by polymerization, i.e. homopolymerization or copolymerization, of at least one olefin in the presence of a catalyst system comprising at least one of the novel organometallic transition metal compounds of the formula (I).

In general, the catalyst system is used together with a further metal compound C') of the formula (X), which may be different from the metal compound(s) C) of the formula (X) used in the preparation of the catalyst system, as constituent of a catalyst system for the polymerization or copolymerization of olefins. The further metal compound is generally added to the monomer or the suspension medium and serves to free the monomer of substances which may adversely affect the catalyst activity. It is also possible for one or more further cation-forming compounds B) to be additionally added to the catalyst system during the polymerization process.

The olefins can be functionalized, olefinically unsaturated compounds such as esters or amide derivatives of acrylic or methacrylic acid, for example acrylates, methacrylates or acrylonitrile, or nonpolar olefinic compounds, including aryl-substituted α-olefins.

Preference is given to polymerizing olefins of the formula $R'''$—CH=CH—$R''$, where $R'''$ and $R''$ are identical or different and are each hydrogen or a carbon-containing radical having from 1 to 20 carbon atoms, in particular from 1 to 10 carbon atoms, and $R'''$ and $R''$ together with the atoms connecting them may form one or more rings.

Examples of such olefins are 1-olefins having from 2 to 40, preferably from 2 to 10 carbon atoms, e.g. ethylene, propylene, 1-butene, 1-pentene, 1-hexene, 1-heptene, 1-octene, 1-decene or 4-methyl-1-pentene, or unsubstituted or substituted vinylaromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene, or cyclic olefins such as norbornene, tetracyclododecene or methylnorbornene.

The catalyst system of the present invention is particularly preferably used for homopolymerizing propylene or ethylene or copolymerizing ethylene with $C_3$-$C_8$-α-olefins such as propylene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidenenorbornene or ethylnorbornadiene or, particularly preferably, for copolymerizing propylene with ethylene and/or 1-butene. Examples of copolymers which can be obtained in this way are propylene-ethylene, propylene-1-butene, ethylene-1-hexene and ethylene-1-octene copolymers and ethylene-propylene-ethylidenenorbornene or ethylene-propylene-1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvents or suspension media, it is possible to use inert hydrocarbons, for example isobutane, or else the monomers themselves.

The polymerizations can be carried out at from −60 to 300° C. and pressures in the range from 0.5 to 3000 bar. Preference is given to temperatures in the range from 50 to 200° C., in particular from 60 to 100° C., at pressures in the range from 5 to 100 bar, in particular from 15 to 70 bar. The mean residence times are usually from 0.5 to 5 hours, preferably from 0.5 to 3 hours. Hydrogen can be used in the polymerization as molar mass regulator and/or to increase the activity. Furthermore, use can also be made of customary additives such as antistatics. The catalyst system of the present invention can be used directly for the polymerization, i.e. it is introduced in pure form into the polymerization system, or it is admixed with inert components such as paraffins, oils or waxes to improve its meterability.

The novel organometallic transition metal compounds of the formula (I) or the catalyst systems in which they are present are very particularly useful for preparing propylene-ethylene copolymers or polypropylene/propylene-ethylene copolymer mixtures.

The invention therefore also provides a process for preparing propylene-ethylene copolymers or polypropylene/propylene-ethylene copolymer mixtures in the presence of a catalyst system as described above.

Ethylene-propylene copolymers having high contents of copolymerized ethylene are obtained at a comparatively low ethylene partial pressure when using the catalyst systems of the present invention.

The invention is illustrated by the following examples which do not, however, restrict the scope of the invention.

EXAMPLES

Examples

Example 1

Synthesis of rac dimethylsilane bis[2-methyl-4-(N-methyl phenylamino)indenyl]zirconium dichloride 1.1 2-Methyl-4-chloroindene

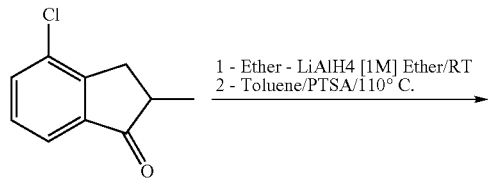

1 - Ether - LiAlH4 [1M] Ether/RT
2 - Toluene/PTSA/110° C.

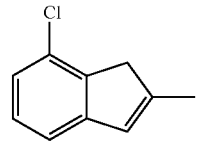

A 1 M solution of LiAlH$_4$ (0.33 eq.) in Et$_2$O was added dropwise to a stirred solution of 2-methyl-4-chloroindanone (20 g, 0.11 mmol) in Et$_2$O (200 ml) at 0° C. for 15 min. The resulting mixture was allowed to warm to room temperature (RT). After 2 h of stirring H$_2$O (100 ml) was added dropwise. The formed layers were separated and the organic phase was washed successively with NH$_4$Cl aq. and NaCl aq. The organic layer was then dried over MgSO$_4$, filtered and concentrated. 19.4 g of a white solid were obtained. The solid was used without further purification. The intermediate alcohol was dissolved in 200 ml toluene. Paratoluene sulfonic acid (PTSA) (0.01 eq.) was added to the resulting stirred solution. Subsequently, the solution was warmed to 120° C. After 5 h of stirring at 120° C. the reaction was cooled down and H$_2$O was added. The formed layers were separated and the organic phase was washed with NaHCO$_3$ and H$_2$O. The organic layer was dried over MgSO$_4$, filtered and concentrated. 16.8 g (92% in two steps) of hell brown oil was obtained. This product was used without further purification.

$^1$H-NMR (400 MHz, CDCl$_3$): δ=7.19-7.06 (m, 3H, aromatic), 6.49-6.48 (bs, 1H, H-Cp), 3.33 (s, 2H, H$_2$-Cp), 2.18 (s, 3H, Me-Cp) ppm.

1.2 2-Methyl-4-(N-methyl phenylamino)indene

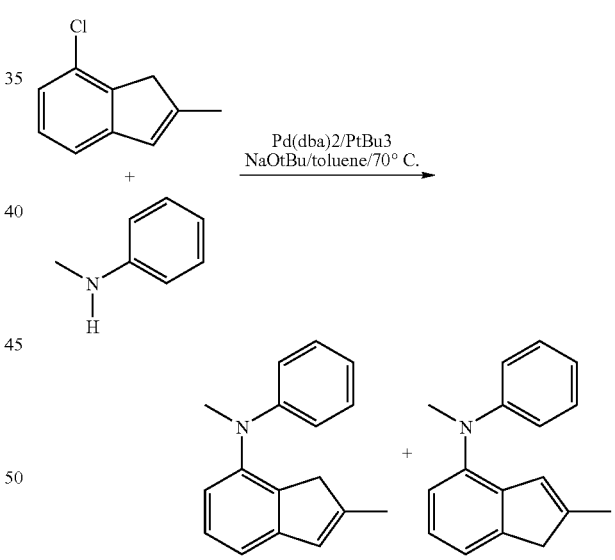

Pd(dba)$_2$ (0.25 g, 0.4 mmol, 1.4 mol %), PtBu$_3$ (0.11 g, 0.5 mmol, 1.8 mol %), NaOtBu (4.5 g, 45.4 mmol, 1.5 eq), 2-methyl-4-chloroindene (5 g, 30 mmol, 1 eq) and N-methyl phenylamine (3.25 g, 30 mmol, 1 eq.) were mixed together and stirred at 70° C. After 2 h of stirring, the reaction was cooled down and H$_2$O was added. The formed layers were separated and the organic phase was washed with NH$_4$C$_1$ and H$_2$O. The organic layer was then dried over MgSO$_4$, filtered and concentrated. Chromatography over SiO$_2$ (Hexan/CH$_2$Cl$_2$:2/1) gave a green oil (4.9 g) in 68% yield.

$^1$H-NMR (400 MHz, CDCl$_3$) of one isomer: δ=7.26-6.70 (m, 8H, aromatic), 6.28 (s, 1H, H-Cp), 3.35 (s, 2H, H$_2$-Cp), 3.33 (s, 3H, Me-N), 2.11 (s, 3H, Me-Cp) ppm

1.3 Bis[2-methyl-4-(N-methyl phenylamino)indene]dimethylsilane

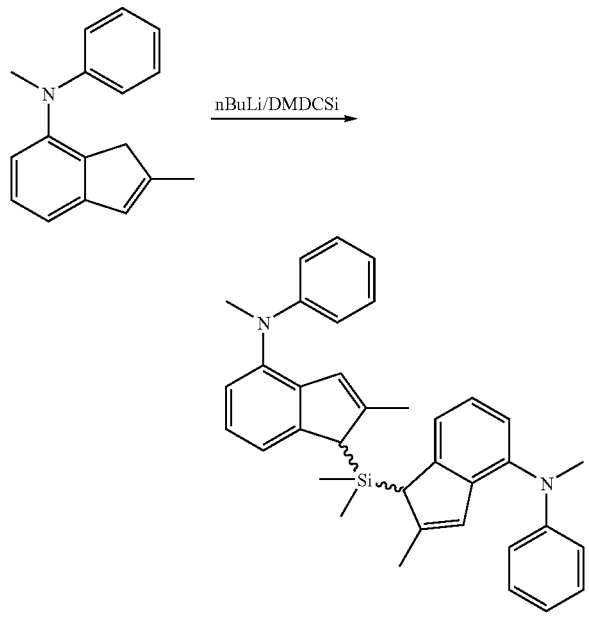

To a stirred solution of 2-methyl-4-(N-methyl phenylamino)indene (4.9 g, 17 mmol) in tetrahydrofurane (THF) (50 ml) at 0° C. was added dropwise a 2.5 M solution of n-butyllithium (n-BuLi) (7.6 ml, 1 eq) in hexane over 10 min. The resulting mixture was allowed to warm to room temperature. After 4 h stirring, dimethyl dichlorosilane (1.15 g, 0.5 eq) was added dropwise. After stirring for 2.5 h, $H_2O$ was added. The formed layers were separated and the organic phase was washed with $NH_4C_1$ and $H_2O$. The organic layer was then dried over $MgSO_4$, filtered and concentrated. Chromatography over $SiO_2$ (Hexan/$CH_2Cl_2$:4/1) gave a white foam (1.5 g) in 27% yield.

$^1$H-NMR (400 MHz, $CDCl_3$) of racemic isomer: δ=7.42-6.66 (m, 16H, aromatic), 6.40 (s, 2H, H-Cp), 3.79 (s, 2H, H-Cp), 3.36 (s, 6H, Me-N), 2.13 (s, 6H, Me-Cp), −0.28 (s, 6H, $(CH_3)_2Si$) ppm.

1.4 Rac/meso dimethylsilane bis[2-methyl-4-(N-methyl phenylamino)indenyl]zirconium dichloride

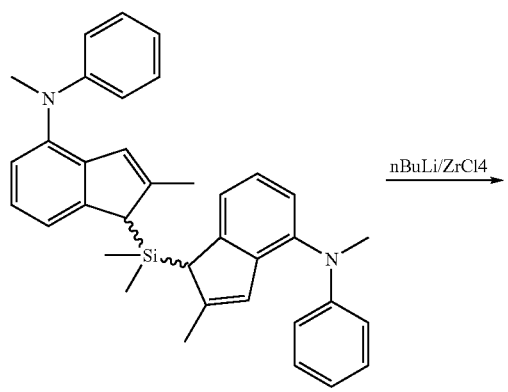

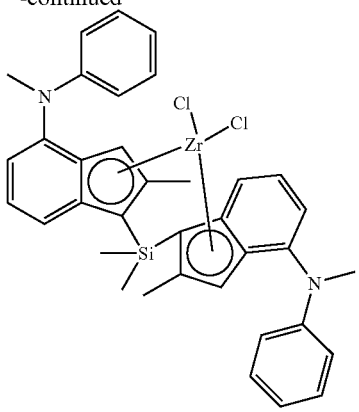

A 2.5 M solution of n-BuLi (0.80 ml, 2 eq) in hexane was added to a stirred solution of bis[2-methyl-4-N-(methyl phenylamino)indene]dimethylsilane (0.52 g, 1 mmol) in $Et_2O$ (5 ml) at 0° C. dropwise for 10 min. The resulting mixture was allowed to warm to room temperature. After 2 h of stirring, a suspension of $ZrCl_4$ (0.231 g, 1 mmol) in pentane was added dropwise. After 15 h stirring, the mixture (rac/meso=1) was filtered and washed with $Et_2O$ (2×1 ml). The red cake was extracted with $CH_2Cl_2$ (30 ml). The mother liquor was concentrated to dryness. The red solid was suspended in THF (5 ml), stirred 2 h at room temperature, filtered and washed with THF (2×1 ml). It gave the racemic form as a red solid (0.085 g) in 12% yield.

$^1$H-NMR (400 MHz, $CDCl_3$ sparingly soluble) of racemic isomer: δ=7.38-6.72 (m, 16H, aromatic), 6.29 (s, 2H, H-Cp), 3.44 (s, 6H, Me-N), 2.16 (s, 6H, Me-Cp), 1.28 (s, 6H, $(CH_3)_2Si$) ppm

1.5 Rac dimethylsilane bis(2-methyl 4-N-methyl phenylamino indenyl)zirconium dichloride

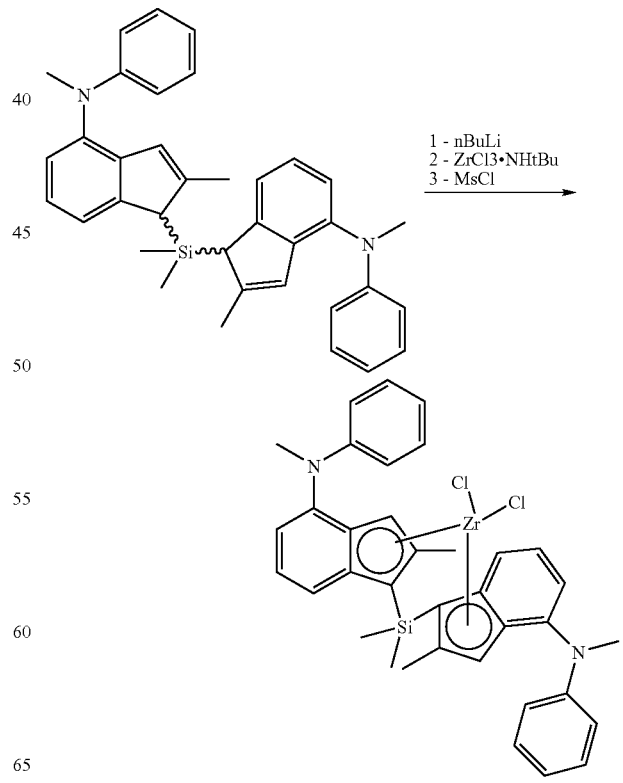

A 2.5 M solution of nBuLi (0.76 ml, 1 eq) in hexane was added dropwise to a stirred solution of t-butylamine (0.15 g, 2 mmol, 1 eq) in toluene (10 ml) and THF (0.14 ml, 1 eq) at 0° C. over 10 mins. The mixture was stirred 1 h at room temperature.

In parallel, to a stirred suspension of ZrCl$_4$ (0.45 g, 1 eq) in toluene (10 ml) was added dropwise at 0° C. THF (0.28 ml, 2 eq).) The mixture was stirred 1 h at room temperature.

The solution of tBuNHLi was added dropwise at room temperature to the suspension of ZrCl$_4$.2THF over 5 mins. The mixture was stirred 1 h at room temperature (ZrCl$_3$.NHtBu.2THF).

In the meantime, a 2.5 M solution of nBuLi (0.34 ml, 2 eq) in hexane was added dropwise to a stirred solution of bis(2-methyl 4-N-methyl phenylamino indene)dimethylsilane in toluene (10 ml) and THF (0.28 ml, 2 eq) over 10 mins. The resulting mixture was allowed to warm to room temperature. After 2 h stirring at room temperature, the ZrCl$_3$NHtBu.2THF suspension was added at room temperature to the dideprotonated ligand over 5 mins. After 15 h stirring, the mixture (rac/meso=7) was filtered and LiCl salts were washed with toluene (2×5 ml). To the stirred orange-red mother liquor was added MsCl (methanesulfonyl chloride) (0.218 g, 1 eq). After 2 h of stirring, the resulting suspension was filtered. The obtained red cake was washed with toluene (2×5 ml) and dried under high vacuum. It gave the racemic form as a red solid (0.31 g) in 24% yield.

$^1$H-NMR (400 MHz, CDCl$_3$) of racemic isomer: see section 1.4

Example 2

Synthesis of rac dimethylsilane bis(2-methyl 4-N,N-diphenylamino indenyl) zirconium dichloride

2.1 2-Methyl-4-(N,N-diphenylamino)indene

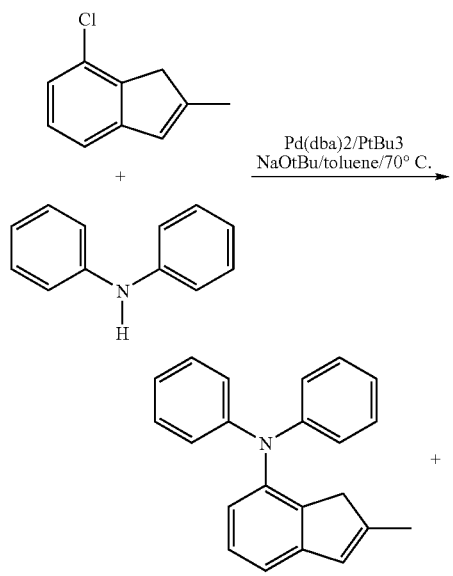

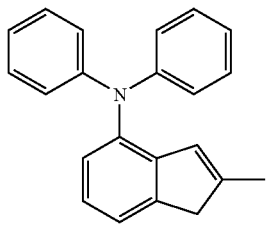

2-Methyl-4-chloroindene was produced as in example 1.1. The preparation of 2-methyl-4-(N,N-diphenylamino)indene was performed in analogous manner to example 1.2 with the exception that instead of N-methyl phenylamine N,N-diphenylamine was used. Chromatography of the crude product over SiO$_2$ (Hexan/CH$_2$Cl$_2$: 4/1) gave a yellow-orange oil (4.8 g) which solidified upon standing at room temperature, in 52% yield.

$^1$H-NMR (400 MHz, CDCl$_3$) of one isomer: 7.27-6.89 (m, 13H, aromatic), 6.44-6.43 (q, J=1.2 Hz, 1H, H-Cp), 2.78 (s, 2H, H$_2$-Cp), 2.02 (bs, 3H, Me-Cp) ppm

2.2 Bis[2-methyl 4-(N,N-diphenylamino)indene]dimethylsilane

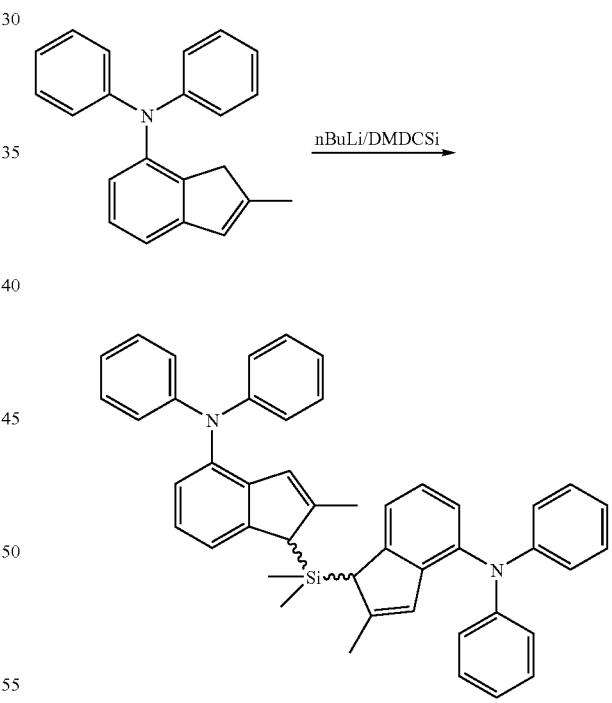

See section 1-3. In this case a mixture toluene/THF (2.5 eq) was used instead of only THF. Moreover, crystallization of the crude product in EtOH (20 ml) gave a white solid (0.52 g) in 48% yield.

$^1$H-NMR (400 MHz, C6D6) of racemic isomer: 7.38-6.68 (m, 26H, aromatic), 6.51 (s, 2H, H-Cp), 3.68 (s, 2H, H-Cp), 1.76 (s, 6H, Me-Cp), −0.32 (s, 6H, (CH$_3$)$_2$Si).

2.3 rac/meso dimethylsilane bis[2-methyl-4-(N,N-diphenylamino)indenyl]zirconium dichloride

2.4 Rac dimethylsilane bis[2-methyl-4-(N,N-diphenylamino)indenyl]zirconium dichloride

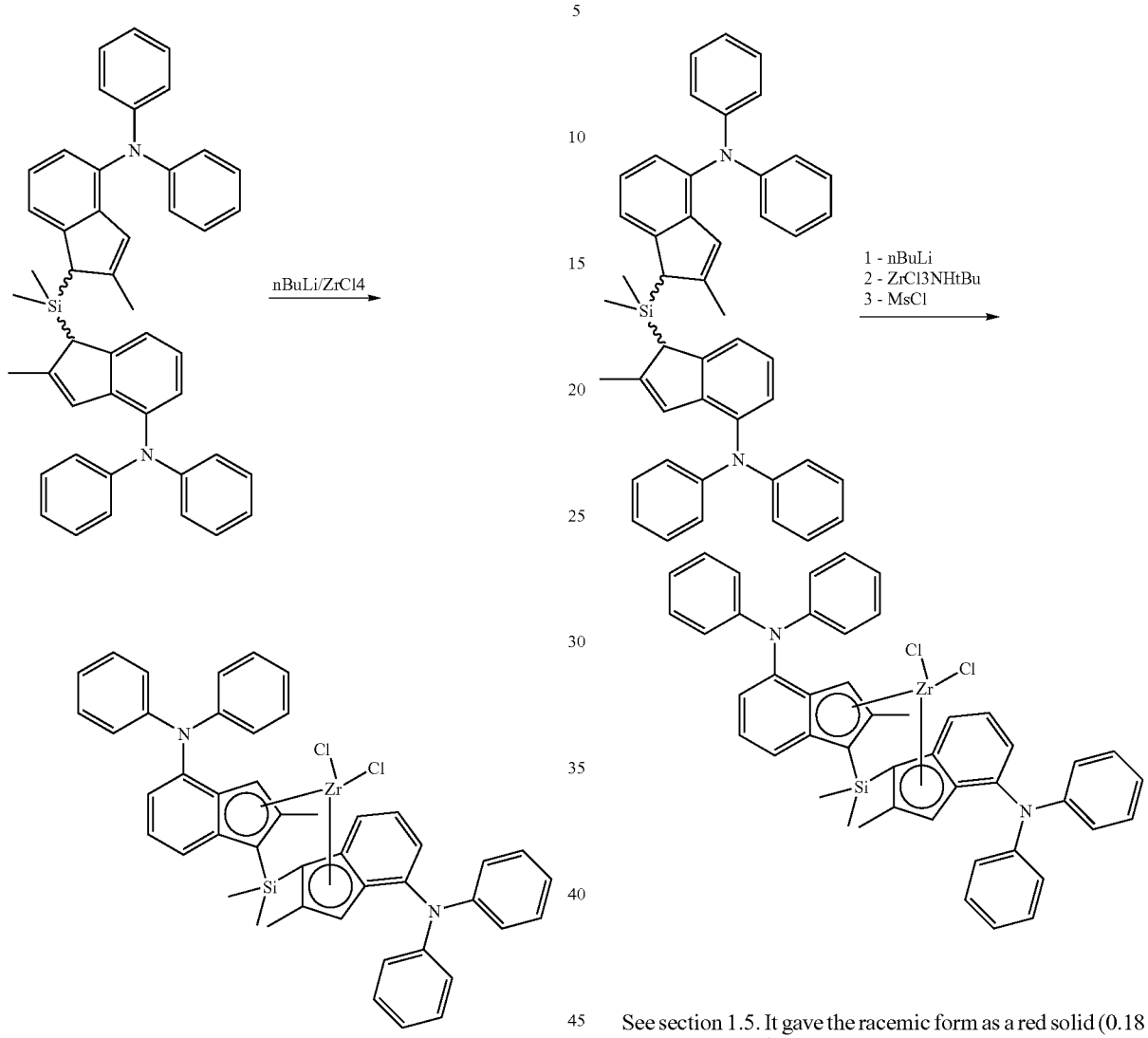

See section 1.5. It gave the racemic form as a red solid (0.18 g) in 20% yield. $^1$H-NMR (C$_6$D$_6$) of racemic isomer: see section 2.3

Example 3

Synthesis of rac dimethylsilane-bis(4-N-methyl phenylamino indacenyl)-zirconiumdichloride

3.1 2-Methyl-4-bromoindacene

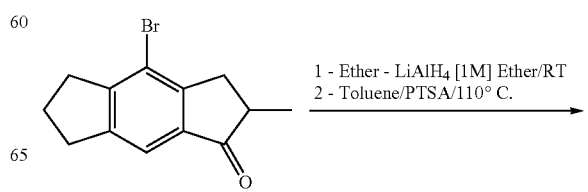

To a stirred solution of bis(4-N,N diphenylamino indene) dimethylsilane (0.70 g, 1.06 mmol) in toluene (10 ml) and THF (0.4 ml) at 0° C. was added dropwise a 2.5 M solution of nBuLi (0.89 ml, 2 eq) in hexane over 10 mins. The resulting mixture was allowed to warm to RT. After 2 h stirring, a suspension of ZrCl$_4$.2THF (0.41 g, 1.08 mmol) in toluene (5 ml) was added. After 15 h stirring, the mixture (rac/meso=1.6) was filtered and LiCl salts were washed with toluene (2×5 ml). During the filtration, the red mother liquor became a suspension. It was stand in the fridge overnight, then filtered and washed with toluene (2×1 ml). It gave the racemic form as a red solid (0.160 g) in 18% yield.

$^1$H-NMR (400 MHz, C$_6$D$_6$) of racemic isomer: 7.32-7.30 (m, 8H, aromatic), 7.13-6.97 (m, 12H, aromatic), 6.86-6.83 (m, 4H, aromatic), 6.66-6.63 (m, 2H, aromatic), 6.34 (s, 2H, H-Cp), 1.92 (s, 6H, Me-Cp), 0.77 (s, 6H, (CH$_3$)$_2$Si).

-continued

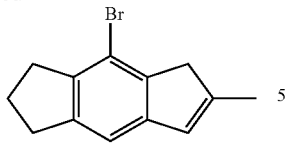

The preparation of 2-Methyl-4-bromoindacene was performed in analogous manner to example 1.1. The organic layer was then dried over MgSO₄, filtered and concentrated. Crystallization of the crude product in MeOH (50 ml) gave a white solid (10.52 g) in 75% yield.

¹H-NMR (400 MHz, CDCl₃): 7.09 (s, 1H, aromatic), 6.46 (s, 1H, H-Cp), 3.24 (s, 2H, H₂-Cp), 3.01 (t, J=6.04 Hz, 2H, C$\underline{H}_2$—CH₂—CH₂), 2.96 (t, J=5.94 Hz, 2H, CH₂—CH₂—C$\underline{H}_2$), 2.15 (s, 3H, Me-Cp), 2.11 (m, 2H, CH₂—C$\underline{H}_2$—CH₂).

3.2 2-Methyl-4-(N-methyl phenylamino)indacene

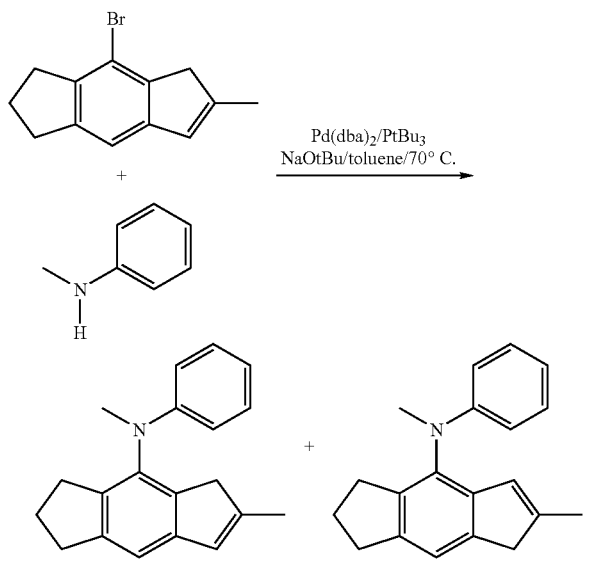

See section 1.2 Chromatography of the crude product over SiO₂ (Hexane/CH₂Cl₂:10/1) gave a yellow oil (3.13 g) in 56% yield.

¹H-NMR (400 MHz, CDCl₃): δ=7.19-7.16 and 6.71-6.54 (m, 5H, aromatic), 7.08 (s, 1H, aromatic), 6.45 (bs, 1H, H-Cp), 3.25 (s, 3H, Me-N), 3.04 (s, 2H, H₂-Cp), 2.96-2.93 (m, 2H, C$\underline{H}_2$—CH₂—CH₂), 2.68-2.63 (m, 2H, CH₂—CH₂—C$\underline{H}_2$), 2.08 (s, 3H, Me-Cp), 2.06-2.04 (m, 2H, CH₂—C$\underline{H}_2$—CH₂) ppm

3.3 bis(2-methyl-4-N methyl phenylamino indacene)dimethylsilane

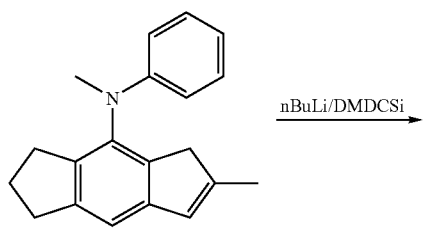

See section 1.3 Crystallization of the crude product in EtOH (20 ml) gave a yellow solid (1.25 g) in 56% yield.

¹H-NMR (400 MHz, CDCl3) of racemic isomer: δ=7.32 (s, 2H, aromatic), 7.20-7.15, 6.71-6.68 and 6.58-6.56 (m, 10H, aromatic), 6.41 (s, 2H, H-Cp), 3.74 (s, 2H, H-Cp), 3.29 (s, 6H, Me-N), 2.97-2.91 (m, 4H, C$\underline{H}_2$—CH₂—CH₂), 2.71-2.64 (m, 4H, CH₂—CH₂—C$\underline{H}_2$), 2.13 (s, 6H, Me-Cp), 2.08-2.04 (m, 4H, CH₂—C$\underline{H}_2$—CH₂), −0.27 (s, 6H, (CH₃)₂Si) ppm.

3.4 rac/meso dimethylsilane bis[2-methyl 4-(N-methyl phenylamino)indacenyl]zirconium dichloride

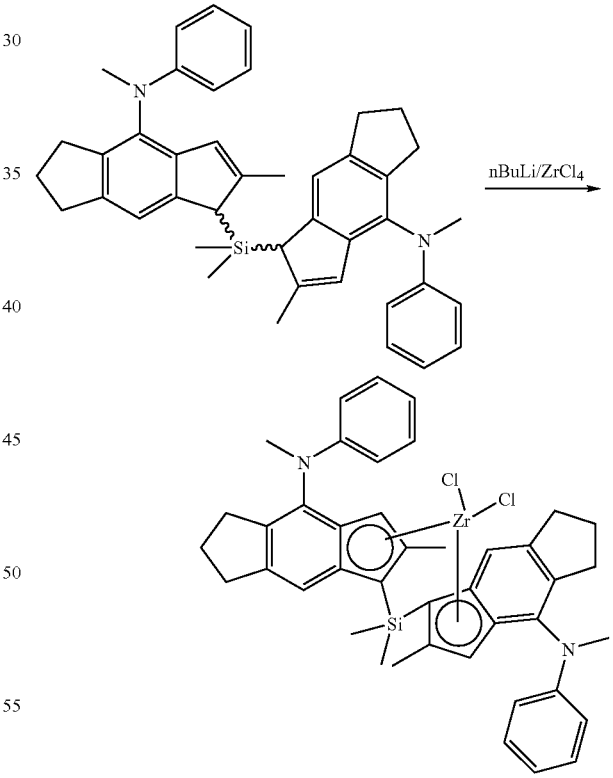

To a stirred solution of bis[2-methyl-4-(N-methyl phenylamino)indacene]dimethylsilane (0.25 g, 0.41 mmol) in toluene (10 ml) and THF (0.1 ml) at 0° C. was added dropwise a 2.5 M solution of nBuLi (0.34 ml, 2 eq) in hexane for 10 min. The resulting mixture was allowed to warm to room temperature. After 2 h of stirring, a suspension of ZrCl₄.2THF (0.16 g, 0.42 mmol) in toluene (5 ml) was added. After 15 h stirring, the mixture (rac/meso=0.9) was filtered and LiCl salts were washed with toluene (2×5 ml). The red mother liquor was concentrated to dryness and treated with acetone (2 ml). The resulting suspension was filtered. The obtained orange cake was washed with acetone (1 ml) and dried under high vacuum. It gave the racemic form as a red solid (0.05 g) in 15% yield.

¹H-NMR (400 MHz, C₆D₆) of racemic isomer: δ=7.31 (s, 2H, aromatic), 7.15-7.10 (m, 4H, aromatic), 6.74-6.73 (m, 2H, aromatic), 6.71 (s, 2H, H-Cp), 6.60-6.59 (d, 4H, aromatic) 3.42 (s, 6H, Me-N), 2.81-2.54 (m, 8H, CH₂—CH₂—CH₂), 1.98 (s, 6H, Me-Cp), 1.81-1.64 (m, 4H, CH₂—CH₂—CH₂), 0.88 (s, 6H, (CH₃)₂Si) ppm Example 4

Synthesis of rac dimethylsilane-bis(4-N,N-diphenylamino indacenyl)-zirconiumdichloride 4.1 2-Methyl-4-(N,N-diphenylamino)indacene

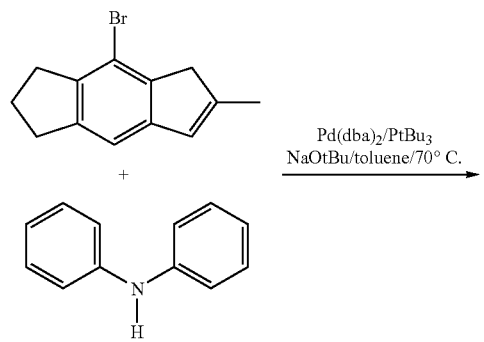

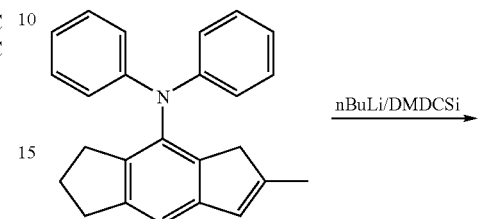

2.52 (m, 2H, CH₂—CH₂—CH₂), 1.83-1.79 (m, 2H, CH₂—CH₂—CH₂), 1.68 (s, 3H, Me-Cp) ppm 4.2 bis(2-methyl-4-(N,N-diphenylamino)indacene) dimethylsilane

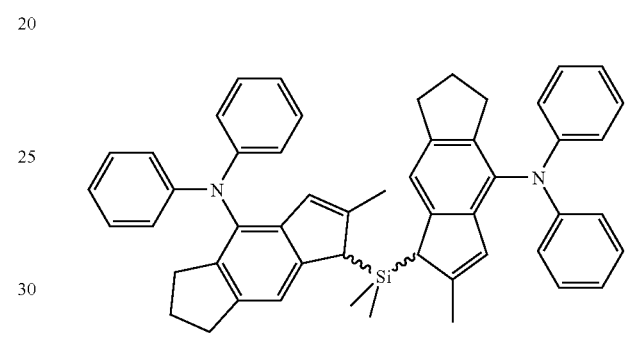

See section 1.3 Crystallization of the crude product in EtOH (20 ml) gave a white solid (3.3 g) in 76.5% yield.

¹H-NMR (400 MHz, C₆D₆) of racemic isomer: δ=7.50 (s, 2H, aromatic), 7.23-7.09 and 6.84-6.81 (m, 20H, aromatic), 6.54 (s, 2H, H-Cp), 3.76 (s, 2H, H-Cp), 2.86-2.80 (m, 4H, CH₂—CH₂—CH₂), 2.64-2.59 (m, 4H, CH₂—CH₂—CH₂), 1.82-1.79 (m, 4H, CH₂—CH₂—CH₂), 1.73 (s, 6H, Me-Cp), −0.29 (s, 6H, (CH₃)₂Si)

4.3 rac dimethylsilane bis[2-methyl 4-(N,N-diphenylamino)indacenyl]zirconium dichloride

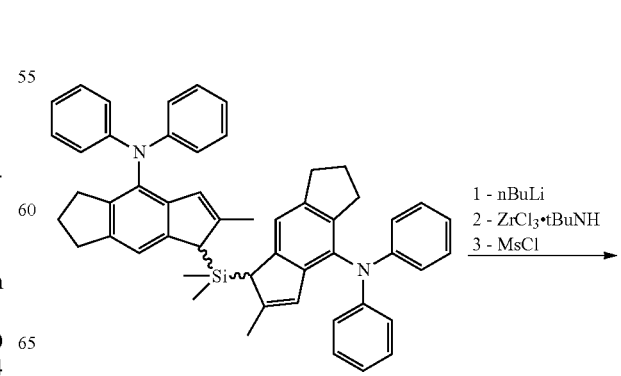

See section 1.2 Crystallization of the crude product in EtOH (20 ml) gave a white solid (4.0 g) in 74.5% yield.

¹H-NMR (400 MHz, C₆D₆) of one isomer: δ=7.15-7.00 and 6.80-6.76 (m, 11H, aromatic), 6.34 (bs, 1H, H-Cp), 2.84 (s, 2H, H₂-Cp), 2.79-2.77 (m, 2H, CH₂—CH₂—CH₂), 2.57-

-continued

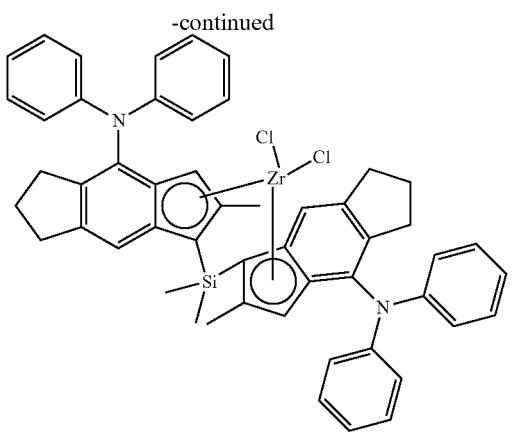

See section 1.5. The obtained orange cake was washed with acetone (1 ml) and dried under high vacuum. It gave the racemic form as an orange solid (0.48 g) in 13% yield.

$^1$H-NMR (400 MHz, $C_6D_6$) of racemic isomer: δ=7.30-7.28 (m, 8H, aromatic), 7.24 (s, 2H, aromatic), 7.11-6.99 (m, 8H, aromatic), 6.84-6.80 (d, 4H, aromatic), 6.55 (s, 2H, H-Cp), 2.60-2.40 (m, 8H, $CH_2$—$CH_2$—$CH_2$), 1.98 (s, 6H, Me-Cp), 1.870-1.62 (m, 4H, $\overline{CH}_2$—$CH_2$—$\overline{CH}_2$), 0.83 (s, 6H, $(CH_3)_2Si$) ppm Polymerization Example P1

P1.1 Synthesis of the Supported Catalyst 95 mmol of metallocene as prepared in example 1 were combined with 1.8 ml of toluene p.a. and the resulting mixture was subsequently stirred for 10 minutes. 4.2 ml of a solution of methylalumoxane in toluene (30% by weight) were added and the suspension was stirred for 1 h. The suspension was added to 4.0 g of silica gel (XPO 2326, Grace; dried at 180° C. for 10 h) during stirring. The suspension was stirred for one hour until no lumps were left and dried to constant weight in a high vacuum.

P1.2 Homopolymerization of Propylene

The homopolymerization was carried out in a 10 l autoclave which had been flushed with nitrogen 3 times. At room temperature 7 ml triethylaluminum 1 molar/L (or tributylaluminum) and 3 kg propylene were introduced. The catalyst was subsequently introduced together with 0.5 kg of propylene. The autoclave was heated to 64° C. within 10 minutes. After 1 h of polymerization the polymerization was stopped by venting.

The polymer was dried overnight under reduced pressure. The results of the polymerization and the results of the analysis of the polymer are shown in table 1 below.

P1.3 Homopolymerization of Propylene with Addition of $H_2$

The polymerization was carried out in a manner analogous to example P1.2 with the exception that 135 mg $H_2$ was added after addition of the alkyl and prior to addition of the propylene.

The results of the polymerization and the results of the polymer analysis are shown in Table 1 below.

P1.4 Copolymerization of Propylene with Ethylene

The homopolymerization was carried out in a 10 l autoclave which had been flushed with nitrogen 3 times. At room temperature 7 ml triethylaluminum 1 molar/L (or tributylaluminum), 0.16 kg ethylene and 3 kg propylene were introduced. The catalyst was subsequently introduced together with 0.5 kg of propylene and the autoclave was heated to 40° C. within 10 minutes. Prepolyerization takes place during a term of 10 min.

Subsequently the autoclave was heated to a temperature of 64° C. within 10 minutes. After 1 h of polymerization the polymerization was stopped by venting.

P2

The polymerizations as described in P1.1 to P1.4 were repeated with the exception that instead of the metallocene as prepared according to example 1 the metallocene of example 2, i.e. rac dimethylsilane bis(2-methyl 4-N,N-diphenylamino indenyl)zirconium dichloride was used.

The resulting polymer was dried overnight under reduced pressure. The results of the polymerization and the results of the analysis of the polymer are shown in table 1 below.

CP3 Comparative Example

The polymerizations as described in P1.1 to P1.4 were repeated with the exception that instead of the metallocene as prepared according to example 1 the rac dimethylsilane bis (2-methyl-4-phenyl indenyl) zirconium dichloride was used.

The resulting polymer was dried overnight under reduced pressure. The results of the polymerization and the results of the analysis of the polymer are shown in table 1 below.

The determination of the molar mass distributions and the means Mn, Mw and Mw/Mn derived therefrom was carried out by high-temperature gel permeation chromatography using a method described in DIN 55672-1:1995-02 issue Februar 1995. The deviations according to the mentioned DIN standard are as follows: Solvent 1,2,4-trichlorobenzene (TCB), temperature of apparatus and solutions 135° C. and as concentration detector a PolymerChar (Valencia, Paterna 46980, Spain) IR-4 infrared detector, capable for use with TCB.

A WATERS Alliance 2000 equipped with the following precolumn SHODEX UT-G and separation columns SHODEX UT 806 M (3×) and SHODEX UT 807 connected in series was used. The solvent was vacuum destilled under Nitrogen and was stabilized with 0.025% by weight of 2,6-di-tert-butyl-4-methylphenol. The flowrate used was 1 ml/min, the injection was 500 μl and polymer concentration was in the range of 0.01%<conc.<0.05% w/w. The molecular weight calibration was established by using monodisperse polystyrene (PS) standards from Polymer Laboratories (now Varian, Inc., Essex Road, Church Stretton, Shropshire, $SY_{6\ 6}AX$, UK) in the range from 580 g/mol up to 11600000 g/mol and additionally Hexadecane. The calibration curve was then adapted to Polyethylene (PE) by means of the Universal Calibration method (Benoit H., Rempp P. and Grubisic Z., & in J. Polymer Sci., Phys. Ed., 5, 753 (1967)). The Mark-Houwing parameters used herefore were for PS: $k_{PS}$=0.000121 dl/g, $α_{PS}$=0.706 and for PE $k_{PE}$=0.000406 dl/g, $α_{PE}$=0.725, valid in TCB at 135° C. Data recording, calibration and calculation was carried out using NTGPC_Control_V6.02.03 and NTGPC_V6.4.24 (hs GmbH, Hauptstraβe 36, D-554370-ber-Hilbersheim) respectively.

The melting temperatures of the polymers ($T_m$) were measured by Differential Scanning Calorimetry (DSC) on a heat flow DSC (TA-Instruments Q2000), according to the standard method (ISO 11357-3 (1999)). The sample holder, an aluminum pan, is loaded with 5 to 6 mg of the specimen and sealed. The sample is then heated from ambient temperature to 200° C. with a heating rate of 20 K/min (first heating). After a holding time of 5 minutes at 200° C., which allows complete melting of the crystallites, the sample is cooled to −10° C. with a cooling rate of 20 K/min and held there for 2 minutes.

Finally the sample is heated from −10° C. to 200° C. with a heating rate of 20 K/min (second heating). The melting temperature is then the temperature ate which the enthalpy versus temperature curve measured during the second heating step displays a maximum.

The $C_2$ content of the propylene-ethylene copolymers was determined by means of $^{13}$C-NMR spectroscopy.

TABLE 1

| Example | $H_2$ [mg] | Ethene [kg] | Activity [kg/(g * h)] | $M_w$ [kg/mol] | Q $M_w/M_n$ | $T_m$ [° C.] | $C_2$-content [Weight %] |
|---|---|---|---|---|---|---|---|
| P1.2 | 0 | 0 | 0.5 | 120 399 | 4.2 | 153.3 | |
| P1.3 | 135 | 0 | 0.7 | 324 570 | 2.5 | 156.0 | |
| P1.4 | 0 | 0.16 | 2.99 | 158 385 | 3.7 | 141.8 | 5% |
| P2.2 | 0 | 0 | 0.1 | 349 645 | 4.6 | 155.4 | |
| P2.3 | 135 | 0 | 0.36 | 305 135 | 3.7 | 154.6 | |
| P2.4 | 0 | 0.16 | 1.37 | 734 216 | 3.5 | 154.2 | 13% |
| CP3.2 | 0 | 0 | 0.8 | 807 805 | 3 | 147.8 | |
| CP3.3 | 135 | 0 | 0.8 | 634 326 | 2.9 | 148.6 | |
| CP3.4 | 0 | 0.16 | 1.85 | 459 007 | 3.2 | 145.1 | 1.6% |

Units and abbreviations: activity in $kg_{polymer}/(g_{transition\ metal\ compound} * h_{polymerization\ time})$; weight average molar mass determined by GPC; polydispersity $Q = M_n/M_w$; ethene content determined by IR spectroscopy

The invention claimed is:

1. A transition metal compound of the formula (I):

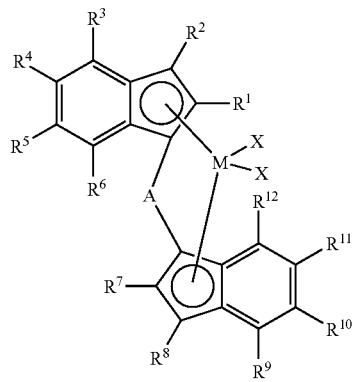

(I)

wherein
M is a Group 4 metal,
$R^3$, $R^4$, $R^9$, and $R^{10}$ are identical or different,
being selected from hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $G^1(R^{13}R^{14})$ and $G^2(R^{13})$, wherein at least one of $R^3$ and $R^4$ is selected from $G^1(R^{13}R^{14})$, $G^1$ is N or P and
$R^1$, $R^2$, $R^5$, $R^6$, $R^7$, $R^5$, $R^{11}$, $R^{12}$
are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, wherein $R^4$ and $R^5$ together with the carbon atoms connecting them may also form a saturated or unsaturated ring system having from 4 to 15 carbon atoms, and wherein $R^{10}$ and $R^{11}$ together with the carbon atoms connecting them may also form a saturated or unsaturated ring system having from 4 to 15 carbon atoms, $R^{13}$ is a $C_1$-$C_{20}$-alkyl, and
$R_{14}$ is a $C_6$-$C_{15}$-aryl, alkylaryl having from 1 to 10 carbon atoms in the alkyl part and from 6 to 20 carbon atoms in the aryl part, arylakyl having from 1 to 10 carbon atoms in the alkyl part and from 6 to 20 carbon atoms in the aryl part, X is halogen, a $C_1$-$C_{20}$-alkyl or a $C_6$-$C_{15}$-aryl,
A represents two substituents as defined for $R^1$ or is a bridge selected from

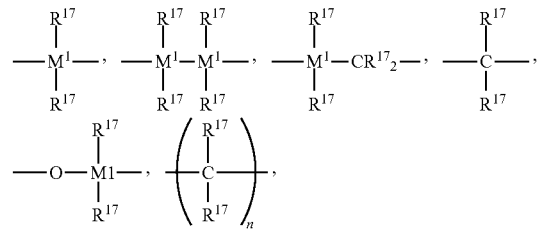

$=BR^{17}$, $=AlR^{17}$, —Ge—, —Sn—, —O—, —S—, $=SO$, $=SO_2$, $=NR^{17}$, $=CO$, $=PR^{17}$ or $=P(O)R^{17}$, wherein
$R^{17}$ are identical or different and are each hydrogen, halogen, $C_1$-$C_{10}$-alkyl, $C_1$-$C_{10}$-fluoroalkyl, $C_6$-$C_{10}$-fluoroaryl, $C_6$-$C_{10}$-aryl, $C_1$-$C_{10}$-alkoxy, $C_2$-$C_{10}$-alkenyl, $C_7$-$C_{40}$-arylalkyl, $C_8$-$C_{40}$-arylalkenyl, $C_7$-$C_{40}$-alkylaryl or two radicals $R^{17}$ together with the atoms connecting them form a ring,
n is an integer from 2 to 6
and
$M^1$ is silicon, germanium or tin.

2. The transition metal compound of claim 1 wherein each of $R^3$ and $R^9$ is $NR^{13}R^{14}$.

3. A catalyst system comprising one or more transition metal compounds of formula (I) as claimed in claim 1 and one or more cocatalysts and/or supports.

4. A process which comprises polymerizing one or more olefins in the presence of the catalyst system of claim 3.

* * * * *